United States Patent
Biddle et al.

(10) Patent No.: US 10,555,832 B2
(45) Date of Patent: Feb. 11, 2020

(54) INTRAOCULAR LENS INJECTOR ASSEMBLY INCLUDING A SHUTTLE AND METHOD OF USING SAME

(71) Applicant: Bausch & Lomb Incorporated, Rochester, NY (US)

(72) Inventors: Graham W. Biddle, Ontario, NY (US); Jon P. Cullen, Churchville, NY (US); Emin Engin, Rochester, NY (US); Bryan M. Reed, Penfield, NY (US); William J. Seyboth, Rochester, NY (US); Moises A. Valle, Tustin, CA (US); Christopher E. Wagner, Webster, NY (US)

(73) Assignee: Bausch & Lomb Incorporated, Rochester, NY (US)

(*) Notice: Subject to any disclaimer, the term of this patent is extended or adjusted under 35 U.S.C. 154(b) by 129 days.

(21) Appl. No.: 15/680,698

(22) Filed: Aug. 18, 2017

(65) Prior Publication Data
US 2017/0340480 A1 Nov. 30, 2017

Related U.S. Application Data

(62) Division of application No. 13/606,362, filed on Sep. 7, 2012, now Pat. No. 9,931,242.

(51) Int. Cl.
*A61F 9/007* (2006.01)
*A61F 2/16* (2006.01)
*A61F 9/00* (2006.01)

(52) U.S. Cl.
CPC ............ *A61F 9/0017* (2013.01); *A61F 2/167* (2013.01); *A61F 2/1662* (2013.01); *A61F 2/1678* (2013.01)

(58) Field of Classification Search
CPC ...... A61F 2/167; A61F 2/1662; A61F 2/1678; A61F 9/0017; A61F 2/1667; A61F 2/1672; A61F 2/1675; A61F 2002/1682
See application file for complete search history.

(56) References Cited

U.S. PATENT DOCUMENTS 5,947,975 A * 9/1999 Kikuchi .............. A61F 2/1664
606/107
RE40,185 E 3/2008 Kikuchi et al.
(Continued)

FOREIGN PATENT DOCUMENTS

CH WO2008098384 A2 8/2008

OTHER PUBLICATIONS

International Search Report and Written Opinion of the International Searching Authority dated Dec. 5, 2013 (13 pages).

*Primary Examiner* — Ahn T Dang
(74) *Attorney, Agent, or Firm* — Timothy W. Menasco, Esq.; Harter Secrest & Emery LLP (57) ABSTRACT

An intraocular lens (IOL) injector assembly comprising an injector body having a shuttle reception opening defined at least in part by a first sidewall and a second sidewall, and a shuttle comprising a first wing including a first portion of a shuttle lumen wall and a second wing including a second portion of a shuttle lumen wall. The first wing and the second wing are coupled together by a hinge. When in a closed state, the first portion of the shuttle lumen wall and the second portion of the shuttle lumen wall define at least a portion of an operative shuttle lumen. The shuttle and sidewalls are configured such that the first wing and the second wing interfere with the first sidewall and the second sidewall, respectively, as the shuttle passes through the shuttle reception opening, such that the closed state of the shuttle is attained.

11 Claims, 6 Drawing Sheets

(56) References Cited

U.S. PATENT DOCUMENTS

| | | | |
|---|---|---|---|
| 2005/0125000 A1* | 6/2005 | Tourrette | A61F 2/1678 |
| | | | 606/107 |
| 2006/0167466 A1 | 7/2006 | Dusek | |
| 2006/0271063 A1 | 11/2006 | Sunada et al. | |
| 2008/0039862 A1 | 2/2008 | Tran | |
| 2008/0221585 A1 | 9/2008 | Downer | |
| 2008/0281333 A1 | 11/2008 | Pessing | |
| 2012/0022547 A1 | 1/2012 | Hildebrand et al. | |

* cited by examiner

INTRAOCULAR LENS INJECTOR ASSEMBLY INCLUDING A SHUTTLE AND METHOD OF USING SAME

FIELD OF INVENTION

The present invention relates to intraocular lens injector assemblies having a shuttle and methods of using the same, and more particularly to intraocular lens injector assemblies having a shuttle that interacts with an injector body to close the shuttle and fold an intraocular lens disposed therein, and methods of using the same.

BACKGROUND OF THE INVENTION

Intraocular lenses (also referred to herein as IOLs or simply as lenses) are artificial lenses used to replace natural crystalline lenses of eyes when the natural lenses are diseased or otherwise impaired. Under some circumstances a natural lens may remain in an eye together with an implanted IOL. IOLs may be placed in either the posterior chamber or the anterior chamber of an eye.

IOLs come in a variety of configurations and materials. Various instruments and methods for implanting such IOLs in an eye are known. Typically, an incision is made in a patient's cornea and an IOL is inserted into the eye through the incision. In one technique, a surgeon uses surgical forceps having opposing blades to grasp the IOL and insert it through the incision into the eye. While this technique is still practiced today, more and more surgeons are using IOL injectors which offer advantages such as affording a surgeon more control when inserting an IOL into an eye and permitting insertion of IOLs through smaller incisions. Smaller incision sizes (e.g., less than about 3 mm) are preferred over larger incisions (e.g., about 3.2 to 5+ mm) since smaller incisions have been associated with to reduced post-surgical healing time and reduced complications such as induced astigmatism.

In order for an IOL to fit through a smaller incision, it is typically folded and/or compressed prior to entering an eye where it will assume its original unfolded/uncompressed shape. Since IOLs are very small and delicate articles of manufacture, great care must be taken in their handling, both as they are loaded into an injector and as they are injected into patients' eyes.

It is important that an IOL be expelled from the tip of the IOL injector and into the eye in an undamaged condition and in a predictable orientation. Should an IOL be damaged or expelled from the injector in an incorrect orientation, a surgeon must remove or further manipulate the IOL in the eye, possibly resulting in trauma to the surrounding tissues of the eye. To achieve proper delivery of an IOL, consistent loading of the IOL into the injector device with a minimum opportunity for damaging the IOL is desirable.

Various IOL injectors and other devices have been proposed which attempt to address issues related to loading, yet there remains a need for an IOL injector which improves consistency of loading and reduces the likelihood of damage to an IOL.

SUMMARY

Aspects of the present invention are directed to an intraocular lens (IOL) injector assembly for folding an IOL comprising an injector body having a shuttle reception opening defined at least in part by a first sidewall and a second sidewall, and a shuttle comprising a first wing including a first portion of a shuttle lumen wall and a second wing including a second portion of a shuttle lumen wall. The first wing and the second wing are coupled together by an at least one hinge. When in a closed state, the first portion of the shuttle lumen wall and the second portion of the shuttle lumen wall define at least a portion of an operative shuttle lumen. The shuttle and sidewalls are sized and shaped such that the first wing and the second wing interfere with the first sidewall and the second sidewall, respectively, as the shuttle passes through the shuttle reception opening, such that, when the shuttle passes through the opening, the closed state of the shuttle is attained. When in the open state, the IOL may be disposed in the shuttle in any suitable state (i.e., an unfolded or a partially folded state), such that when the closed state is attained, the IOL is folded from the state the IOL was in when the shuttle was in the open state in preparation for ejection of the IOL from the injector into an eye.

In some embodiments, the assembly further comprises a third portion of the shuttle lumen, the first wing portion coupled to the third portion by the first hinge and the second wing portion being coupled to the third portion by a second hinge.

The shuttle may have an open state in which the IOL is maintained in the shuttle in a substantially unstressed state. The shuttle may comprise a handle for facilitating insertion of the shuttle into the opening.

In some embodiments, each of the shuttle and the sidewalls comprises at least one interference feature. In some embodiments, each of the wings and each of the sidewalls comprises at least one interference feature. The interference feature may be a ramp.

In some embodiments, the first wing comprises a first interference feature, the second wing comprises a second interference feature, the first sidewall comprises a third interference feature and the second sidewall comprises a fourth interference feature. Each of the interference features may be a ramp.

The injector body may comprise a nozzle integrally formed therewith.

The shuttle may comprise a locking feature to maintain the shuttle in the closed state.

In some embodiments, the assembly comprises a nozzle having a nozzle lumen, and wherein the assembly is capable of achieving a state in which the operative shuttle lumen is aligned with the nozzle lumen.

Another aspect of the invention is directed to a method of assembling an intraocular lens (IOL) injector. The method comprises providing an injector body having a shuttle reception opening defined at least in part by a first sidewall and a second sidewall, providing a shuttle comprising a first wing including a first portion of a shuttle lumen wall and a second wing including a second portion of a shuttle lumen wall, the first wing and the second wing being coupled together by an at least one hinge, and inserting the shuttle into the shuttle reception opening thereby interfering the first side wall with the first wing and the second side wall with the second wing. Prior to said interfering, the shuttle is in an open state. When in the open state, an IOL may be disposed in the shuttle in any suitable state (i.e., an unfolded or a partially folded state), such that when the closed state is attained, the IOL is folded from the state the IOL was in when the shuttle was in the open state in preparation for ejection of the IOL from the injector into an eye.

The step of inserting may cause the shuttle to achieve a closed state, whereby the first portion of the shuttle lumen wall and the second portion of the shuttle lumen wall define at least a portion of an operative shuttle lumen.

The first wing may comprise a first interference feature, the second wing comprises a second interference feature, the first sidewall comprises a third interference feature and the second sidewall comprises a fourth interference feature.

Each of the wings and each of the sidewalls may comprise at least one interference feature.

In some instances, during the step of inserting, interfering the first interference feature with the third interference feature and interfering the second interference feature with the fourth interference feature.

Another aspect of the invention is directed to an intraocular lens shuttle, comprising a first wing including a first portion of a shuttle lumen wall, a second wing including a second portion of a shuttle lumen wall, the first wing and the second wing being coupled together by an at least one hinge and, when in a closed state, the first portion of the shuttle lumen wall and the second portion of the shuttle lumen wall define at least a portion of a shuttle lumen, the shuttle lumen being operative, and a handle coupled to the first wing and the second wing which permits the wings to move between an open state and the closed state.

In some embodiments, the shuttle further comprising a third portion of the shuttle lumen, the first wing portion coupled the third portion by a first hinge of the at least one hinge and the second wing portion being coupled to the third portion by a second hinge of the at least one hinge.

The handle may be disposed above and over at least a part of the lumen. The handle may be disposed opposite the at least one hinge.

In some embodiments, at least one of the first wing and the second wing comprises an interference feature.

The shuttle may be in the open state and include an IOL in a substantially unstressed state disposed on the shuttle lumen wall.

Yet another aspect of the invention is directed to an intraocular lens shuttle, comprising a first wing including a first portion of a shuttle lumen wall, a second wing including a second portion of a shuttle lumen wall, the first wing and the second wing being coupled together by an at least one hinge and, when in a closed state, the first portion of the shuttle lumen wall and the second portion of the shuttle lumen wall define at least a portion of a shuttle lumen, the shuttle lumen being operative, and at least one of the first wing and the second wing comprises an interference feature as set forth herein.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Figure 1:
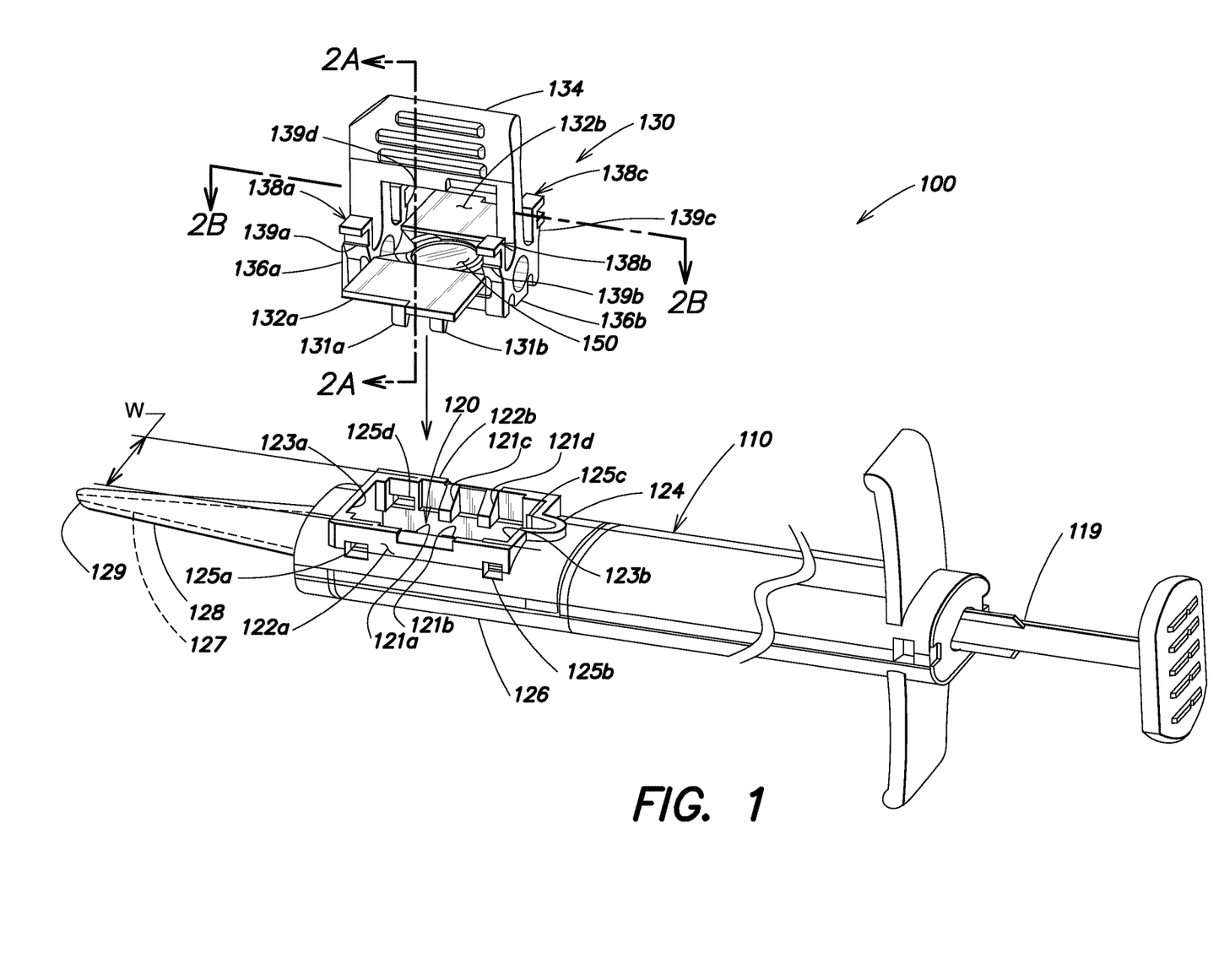
FIG. 1 is a schematic view of an example of an embodiment of an intraocular lens (IOL) injector assembly according to aspects of the present invention including an injector body and a shuttle, where the shuttle is in an open state.
Figure 2A:
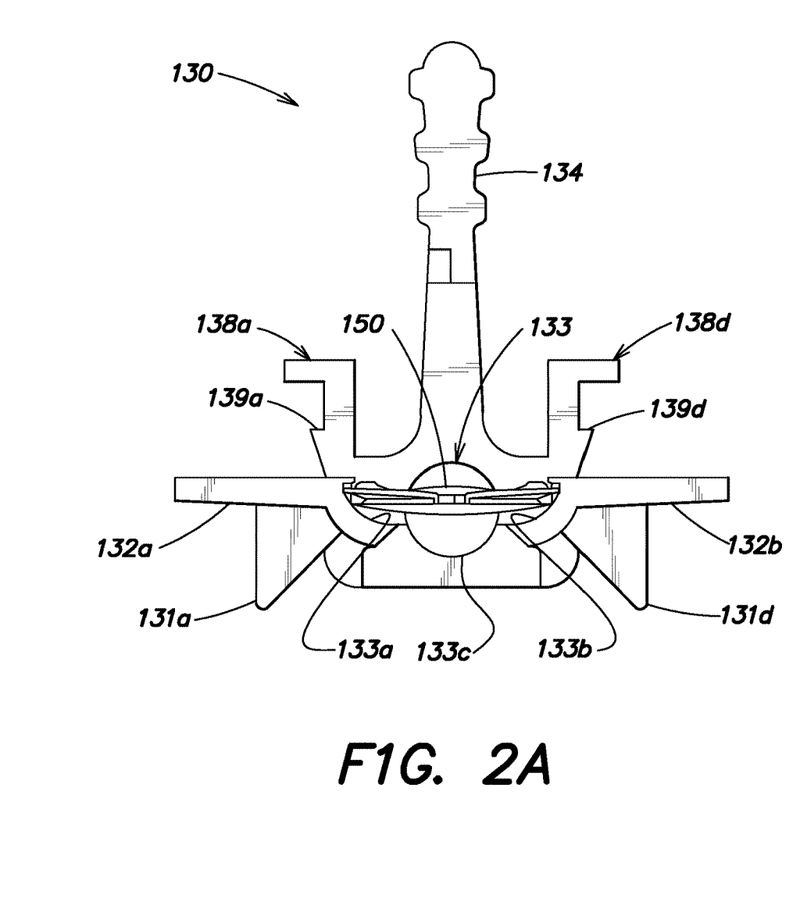
FIG. 2A is a rear cross sectional view of the shuttle of FIG. 1 taken along line 2A-2A, where the shuttle is in an open state.
Figure 2B:
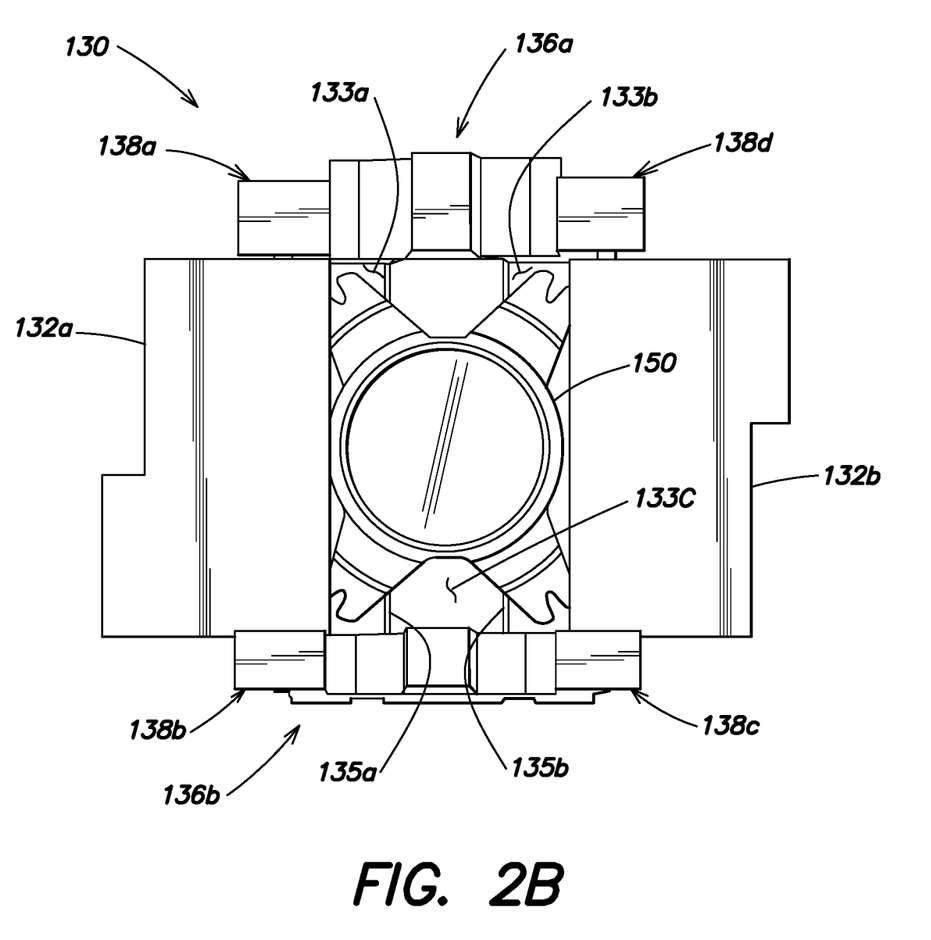
FIG. 2B is a top view of the shuttle of FIG. 1 taken along line 2B-2B, where the shuttle is in an open state.
Figure 2C:
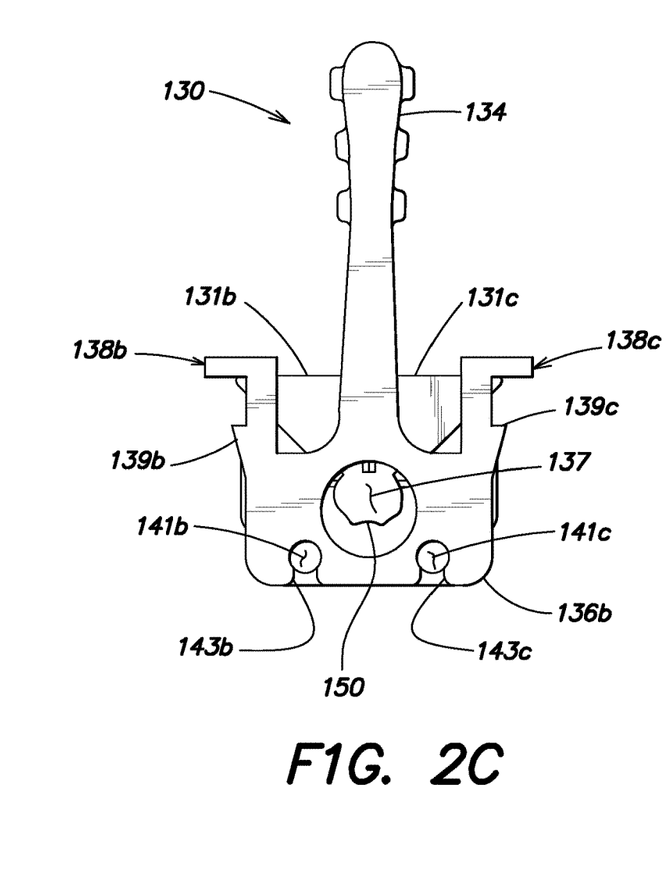
FIG. 2C is a rear view of the shuttle of FIG. 1, where the shuttle is in a closed state.

FIG. 1 is a schematic view of an example of an embodiment of an intraocular lens (IOL) injector assembly 100 according to aspects of the invention that includes an injector body 110 and a shuttle 130, where the shuttle is in an open state. FIG. 2A is a rear cross sectional view of shuttle 130 of FIG. 1 taken along line 2A-2A. FIG. 2B is a top view of shuttle 130 of FIG. 1 taken along line 2B-2B. FIG. 2C is a rear view of shuttle 130 of FIG. 1, when the shuttle is in a closed state. The first example of an embodiment of an IOL injector according to aspects of the present invention will be discussed with reference to FIGS. 1 and 2A-2C.

Shuttle 130 for holding an IOL 150 comprises a first wing 132*a* including a first portion of a shuttle lumen wall 133*a* and a second wing 132*b* including a second portion of the shuttle lumen wall 133*b*. The first wing 132*a* and the second wing 132*b* are coupled together by at least one hinge 135*a*, 135*b*. The at least one hinge permits rotational movement of wings 132*a* and 132*b* between an open position and a closed position. In the illustrated embodiment of a shuttle, the first wing 132*a* and the second wing 132*b* are coupled together by two hinges 135*a*, 135*b*.

In the illustrated embodiment, the open position permits the lens to sit within the shuttle disposed on a portion of the shuttle wall in an unstressed (i.e., unfolded) position which can be useful for maintaining shelf life of the IOL when it is packaged awaiting implantation into an eye. An IOL may be hydrophilic or hydrophobic. It will be appreciated that for a hydrophobic lens, in addition to meeting any sterile packaging requirements, the packaging will include an amount of hydrating solution to maintain the lens.

When the shuttle 130 is in the closed state, the first portion of the shuttle lumen wall 133*a* and the second portion of the second lumen wall 133*b* define at least a portion of an operative shuttle lumen 137. In the illustrated embodiment, a third portion of the lumen wall 133*c* is located between hinges 135*a* and 135*b*. First wing 132*a* is coupled to the third portion 133*c* by first hinge 135*a* and the second wing 132*b* is coupled to the third portion 133*c* by a second hinge. When the shuttle is in the closed state portions 133*a*, 133*b*, 133*c* define the operative lumen 137. An operative lumen is sufficiently complete to guide a lens and to avoid damage to the lens as it passes therethrough. In the closed state, portions 133*a*, 133*b*, 133*c*, in cross section, may form a completely closed shape.

To facilitate handling of the shuttle, including handling to place the shuttle and lens into an injector body for injection into an eye, shuttle 130 is provided with a carrier structure including a handle 134 and handle attachment portions 136*a* and 136*b* at the ends which connect the handle to the remainder of the shuttle and permit rotational movement of wings 132*a* and 132*b*. In the illustrated embodiment, end portions include shuttle attachment portions 138*a*-138*d* for connecting to the injector body and supporting the shuttle. In the illustrated embodiment, the handle extends above and over at least one of the lumen walls 133; and in some embodiments is opposite the at least one hinge. A locking ledge 139*a*-139*d* on each attachment portion fits into a corresponding locking hole 125*a*-125*d* to form an interference lock once locking ledges 139*a*-139*d* enter holes 125*a*-125*d* which prevents removal of the shuttle once it is connected to the injector body and maintains alignment of shuttle lumen 137 and nozzle lumen 127 as set forth below.

Injector body 110 has a shuttle reception opening 120 defined at least in part by a first sidewall 122*a* and a second sidewall 122*b*. As described in greater detail below, the shuttle wing 132*a* and shuttle wing 132*b* interfere with the first sidewall 122*a* and second sidewall 122*b*, respectively, as the shuttle is inserted into the shuttle reception opening 120 thereby causing the shuttle to attain a closed state. One or more interference features may be added to shuttle 130 and/or sidewalls 122*a*, 122*b* to facilitate closing. An interference feature comprises a protuberance. For example, in the illustrated embodiment of an assembly, ramps 131*a*-131*d* are added to the wings of the shuttle, and ramps 121*a*-121*d* are added to the sidewalls. As described in greater detail below, when the shuttle 130 passes through the opening 120, the closed state of the shuttle is attained.

In the illustrated embodiment, a proximal wall 123*a* and a distal wall 123*b* in the injector body further define the opening 120. A contour is formed in proximal wall 123*a* which forms a viscoelastic port through which viscoelastic can be added to the shuttle and lens 150 after the shuttle and lens 150 are connected to the injector body at opening 120. In the illustrated embodiment, the injector body includes several portions: a plunger 119, a nozzle 128 with a nozzle lumen 127 and with a distal opening 129 through which an IOL is delivered into an incision in an eye as discussed in greater detail below, and a main body portion 126 which serves is the primary portion by which the injector is held by a user and primary portion by which the remaining portions are supported. The nozzle and the remainder of the injector body may be constructed as a single integrated unit (i.e., they are manufactured and formed as a single unit); however, it will be appreciated that in some embodiments, the nozzle is produced as a separate piece that is coupled to the remainder of the injector body to form the injector body. Also, in some embodiments in which the nozzle is manufactured as a separate component, the nozzle includes sidewalls 122*a* and 122*b*, and opening 120. For example, the nozzle may be produced as a separate piece to facilitate manufacture of components or to facilitate different handling and shelf lives of the nozzle and remaining injector body components. The plunger may be a slidable-type plunger or a screw-type plunger. The plunger is adapted to eject an IOL from the shuttle and the distal opening in the nozzle after the closed state is attained.

In some embodiments, it is advantageous if the shuttle is manufactured as two components: a frame component comprising handle 134 and handle attachment portions 136*a* and 136*b*; and a second component comprising first wing 132*a*, second wing 132*b*, and third portion 133*c*, including hinges 135*a* and 135*b*. The frame component and second component can be coupled together in any suitable manner. As shown, the second component may be provided with extensions 141*b* and 141*c* that are snapped into receptacles 143*b* and 143*c* in the frame component. It will be appreciated that additional extensions 143*a* and 143*d*, and receptacles 143*a* and 143*d* (which are not visible) are provided on the opposite side of the shuttle 130.

Figure 3:
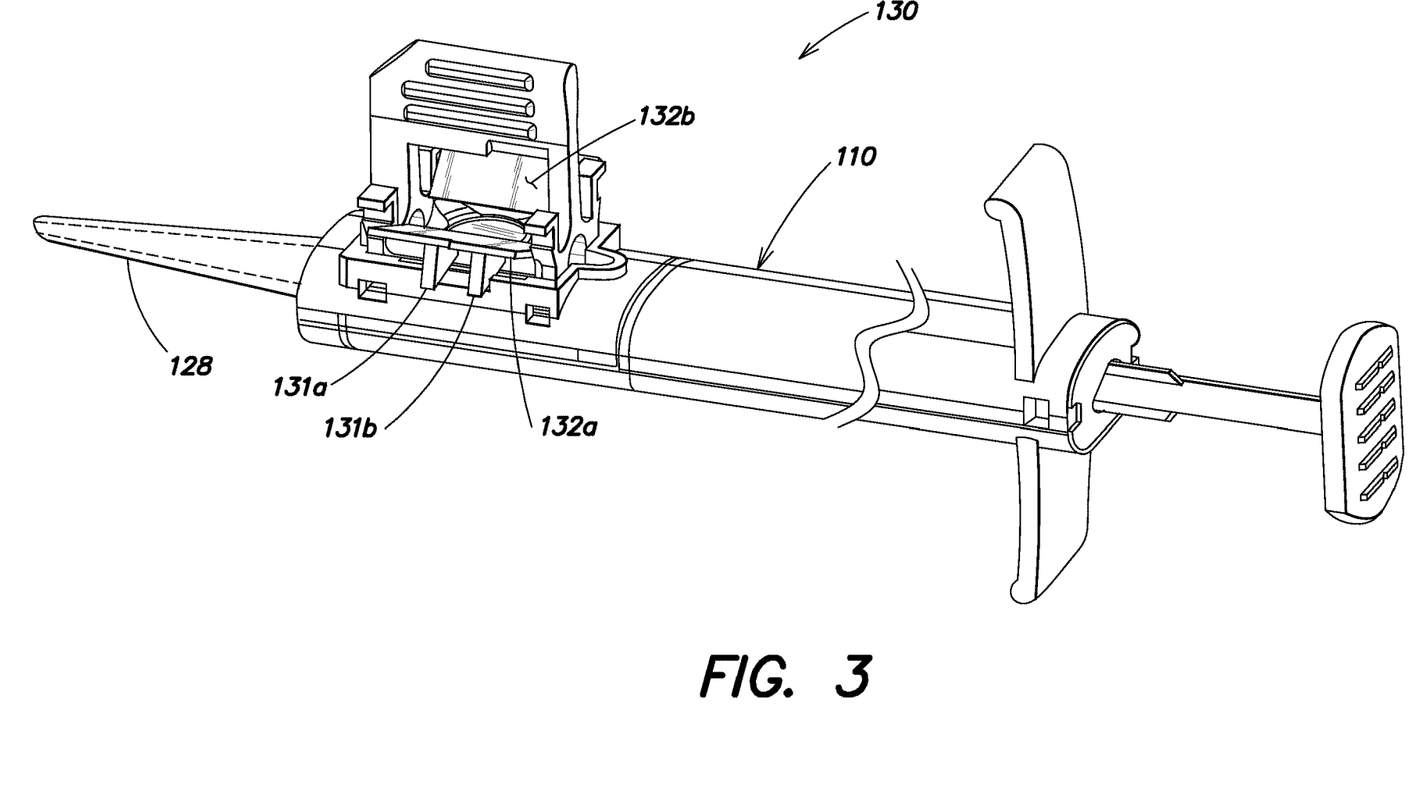
FIG. 3 is a partial, schematic view of the injector assembly of FIG. 1 when the shuttle begins to enter the shuttle reception opening.

FIG. 3 is a partial, schematic view of the injector assembly of FIG. 1 where the shuttle begins to enter the shuttle reception opening. The shuttle 130 and sidewalls 122*a*, 122*b* are sized and shaped such that the first wing 132*a* and the second wing 132*b* interfere with the first sidewall 122*a* and the second sidewall 122*b*, respectively, as the shuttle 130 passes through the shuttle reception opening 120. The width W of opening 120 is sized relative to the wings such that shuttle wing 132*a* and shuttle wing 132*b* interfere with the first sidewall 122*a* and second sidewall 122*b*, respectively, as the shuttle is inserted into the shuttle reception opening 120. As described above, one or more features may be added to shuttle 130 and/or sidewalls 122*a*, 122*b* to facilitate closing. A need for interference features one or more of the shuttle and the sidewalls depends on the dimensions of the shuttle and the opening 120. For example, ramps 131*a*-131*d* may be added to the wings of the shuttle, and ramps 121*a*-121*d* may be added to the sidewalls. In the illustrated embodiment, the width W of opening 120 (including the locations of ramps 121*a*-121*d*) is sized relative to the location of the wings such that ramps 131*a*-131*d* on shuttle wings 132*a* and 132*b* interfere with the ramps 121*a*-121*d* on the shuttle body. It will be appreciated that, although ramps 121*a*-121*d* and 131*a*-132*d* are shown, any suitably-shaped interference feature may be provided to achieve interference such that a closed state of the shuttle is achieved when the shuttle passes through opening 120. Although the illustrated embodiment is shown with four interference features on the shuttle wings (i.e., two interference features on each wing) and four interference features (e.g., ramps) on the injector body (e.g., sidewalls), one or more features on each wing and one or more features on each sidewall may be appropriate. It will also be appreciated that the interference features on the shuttle interferes with corresponding interference features on the injector body as the shuttle enters shuttle reception opening 120. Interference of the various interference features on the shuttle with interference features on the injector body may occur simultaneously.

Figure 4:
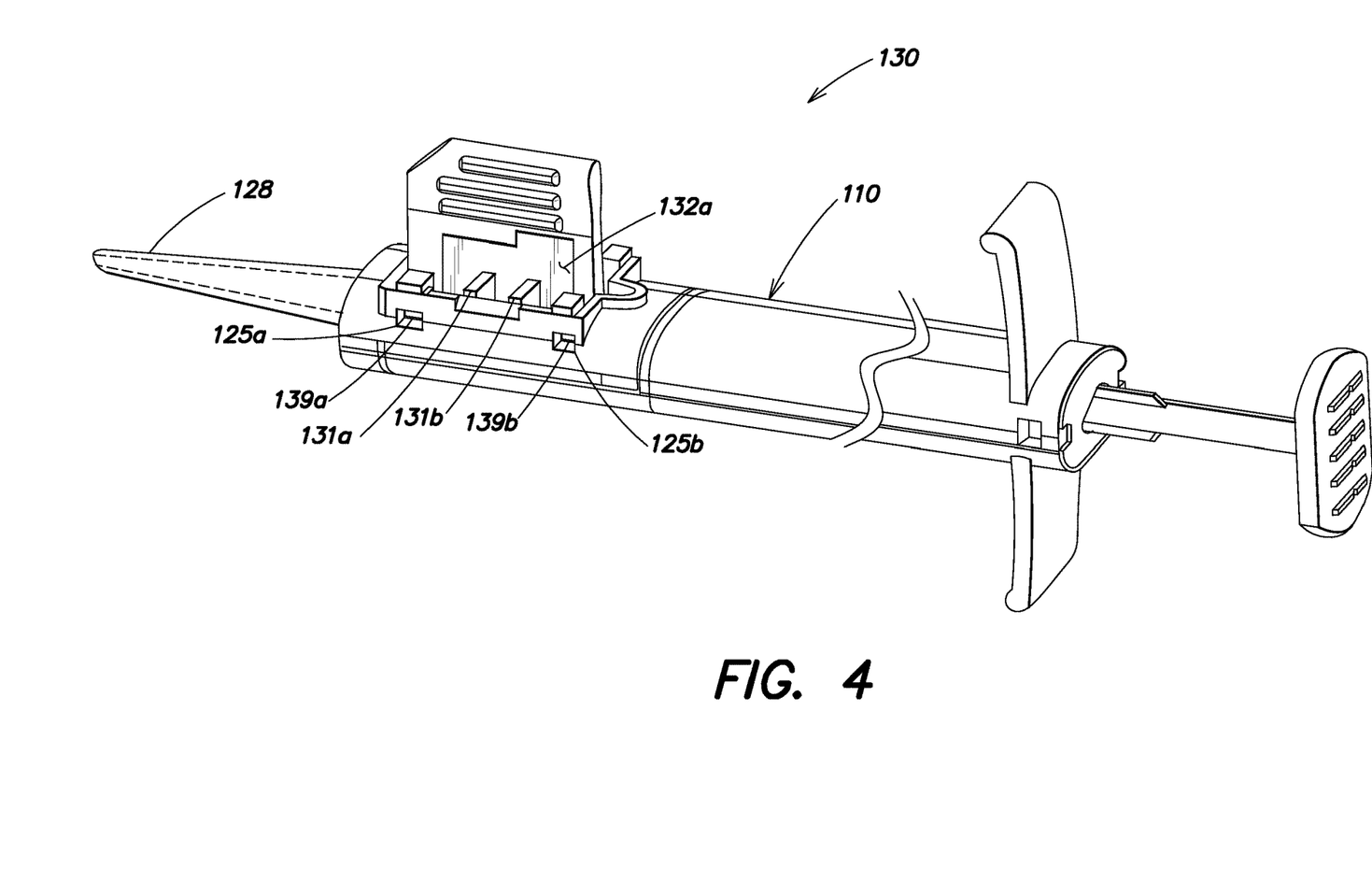
FIG. 4 is a partial, schematic view of the injector assembly of FIG. 1 when the shuttle is fully within the reception opening and the shuttle is in a closed state.

FIG. 4 is a partial, schematic view of the injector assembly of FIG. 1 when the shuttle is fully within the reception opening and the shuttle is in a closed state. When the shuttle 130 passes through the opening 120, the closed state of the shuttle is attained. Locking features may be included on the wings or other portions of the shuttle so that the shuttle is locked in the closed state after closure. For example, the wings may have interference or snap feature on the ends of the wings, or the wings may be magnetized, contain Velcro, require electronic actuation or any other suitable means for locking the shuttle in a closed state.

The closed state is best shown in FIG. 2C where a folded IOL 150 is included therein. In the injector state shown in FIG. 3, shuttle lumen 137 is aligned with the nozzle lumen 127 such that actuation of plunger 119 results in expulsion of the IOL from distal opening 129. It will be appreciated that nozzle 128 may provide additional folding of IOL 150 beyond what is achieved by closing shuttle 130, such that upon actuation of the plunger, the IOL is further folded by internal shape of the nozzle lumen as the IOL passes therethrough. Locking ledges 139*a*-139*d* are disposed in corresponding locking hole 125*a*-125*d* which inhibits removal of the shuttle from the injector body.

Figure 5:
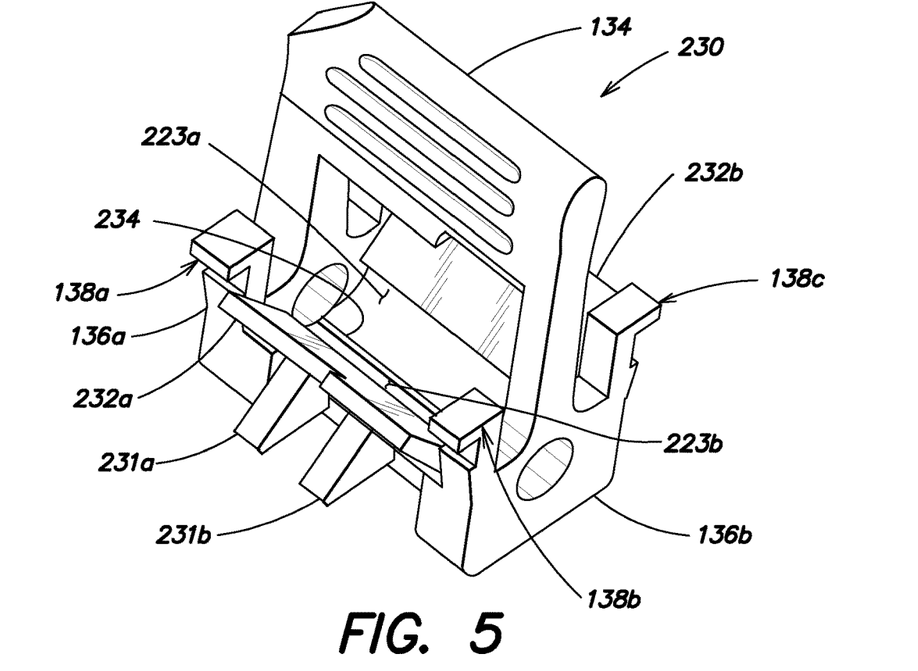
FIG. 5 is a schematic view of another example of an embodiment of a shuttle according to aspects of the present invention for use in an intraocular lens IOL injector assembly.

FIG. 5 is a schematic view of another example of an embodiment of a shuttle 230 according to aspects of the present invention for use in an intraocular lens IOL injector assembly. Shuttle 230 is similar in construction and function to shuttle 130 discussed above; however, shuttle 230 comprises only a single hinge 234.

Similar to shuttle 130, to facilitate handling of the shuttle, shuttle 130 includes a carrier structure including a handle 134 and handle portions 136a and 136b which permit rotation movement of wings 232a and 232b. Wings 232a and 232b comprise a portion of shuttle lumen wall 223a and a portion of shuttle lumen wall 223b, respectively. In the illustrated embodiment, end portions include shuttle attachment portions 138a-138d (attachment portion 138c is not visible in FIG. 5) for connecting to the injector body and supporting the shuttle. For the illustrated embodiment, when in a closed state (not shown), portion of shuttle lumen wall 223a and portion of shuttle lumen wall 223b define an operative shuttle lumen. For the illustrated embodiment, in cross section, portion of shuttle lumen wall 223a and portion of shuttle lumen wall 223b form a closed shape when the shuttle is in a closed state.

Figure 6:
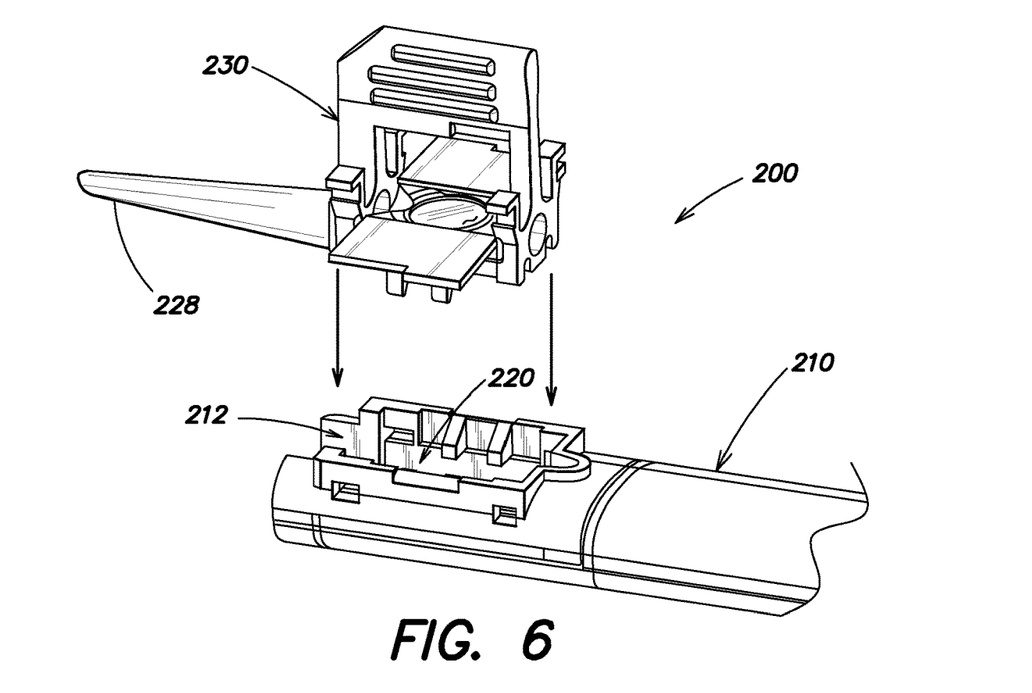
FIG. 6 is a partial, schematic view of yet another example of an embodiment of an intraocular lens IOL injector assembly according to aspects of the invention including an injector body and a shuttle having an injector nozzle connected thereto, illustrating the shuttle is in an open state.

FIG. 6 is a schematic view of yet another example of an embodiment of an intraocular lens IOL injector assembly 200 according to aspects of the invention. Assembly 200 includes an injector body 210 and a shuttle 230; however, unlike in assembly 100 discussed above, shuttle 230 has an injector nozzle 228 connected thereto, rather than the nozzle being connected to the injector body. Injector body 210 has a notch 212 to accommodate the nozzle when shuttle 230 is attached to injector body 210. Shuttle 230 is sized and shaped relative to opening 220 in injector body 210 such that, other than the nozzle being attached to the shuttle rather than the injector body, the assembly 200 functions substantially the same as assembly 100 to close shuttle 230 as the shuttle 130 passes through the shuttle reception opening 220.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

The invention claimed is:

1. A method of assembling an intraocular lens (IOL) injector, comprising:
   providing an injector body having a plunger and a shuttle reception opening that is formed into and along a length of the injector body, and is defined at least in part by a first sidewall and an opposed second sidewall;
   providing a shuttle that is a separate piece from the injector body and is insertable into the shuttle reception opening, the shuttle comprising:
      a first wing including a first portion of a shuttle lumen wall;
      a second wing including a second portion of a shuttle lumen wall, the first wing and the second wing being coupled together by an at least one hinge; and
      a frame comprising a handle for facilitating insertion of the shuttle into the shuttle reception opening, the handle extending between ends of the shuttle and connecting handle attachment portions formed at the ends of the frame, the handle being disposed above and between the first and second wings to permit the wings to move between an open state and a closed state; and
   inserting the shuttle into the shuttle reception opening, the shuttle, the first sidewall, and the opposed second sidewall being sized and shaped such that the first wing and the second wing interfere with the first sidewall and the opposed second sidewall, respectively, and
   wherein, upon insertion and when in the closed state, the first portion of the shuttle lumen wall and the second portion of the shuttle lumen wall define at least a portion of an operative shuttle lumen that is sized for receiving and holding the IOL.

2. The method of claim 1, wherein the first wing comprises a first interference feature, the second wing comprises a second interference feature, the first sidewall comprises a third interference feature and the opposed second sidewall comprises a fourth interference feature.

3. The method of claim 1, wherein each of the wings and each of the sidewalls comprises at least one interference feature.

4. The method of claim 2 wherein, during the step of inserting, interfering the first interference feature with the third interference feature and interfering the second interference feature with the fourth interference feature.

5. The method of claim 2, wherein each of the first, second, third, and fourth interference features is a ramp.

6. The method of claim 3, wherein the at least one interference feature is a ramp.

7. The method of claim 1, wherein the shuttle is in the closed state prior to the interference between the wings and the side walls.

8. The method of claim 7, wherein, as the shuttle is inserted into the shuttle reception opening, the closed state of the shuttle is attained.

9. The method of claim 1, wherein the plunger includes a nozzle integrally formed therewith.

10. The method of claim 1, wherein the open state in which the IOL is configured to be maintained in the shuttle is in a substantially unstressed state.

11. The method of claim 1, wherein the shuttle comprises a locking feature to maintain the shuttle in the closed state.

\* \* \* \* \*